(12) United States Patent
Von Blücher et al.

(10) Patent No.: US 8,491,892 B2
(45) Date of Patent: Jul. 23, 2013

(54) ACTIVATED CARBON FOR MEDICAL USE

(75) Inventors: Hasso Von Blücher, Erkrath (DE);
Oliver Böhm, Bad Homberg (DE);
Michael Klemund, Düsseldorf (DE)

(73) Assignee: Blucher GmbH, Erkrath (DE)

( * ) Notice: Subject to any disclaimer, the term of this patent is extended or adjusted under 35 U.S.C. 154(b) by 642 days.

(21) Appl. No.: 11/640,633

(22) Filed: Dec. 18, 2006

(65) Prior Publication Data

US 2007/0141046 A1    Jun. 21, 2007

(30) Foreign Application Priority Data

Dec. 19, 2005  (DE) .......................... 10 2005 061 120
Dec. 22, 2005  (DE) .......................... 10 2005 062 160

(51) Int. Cl.
*A61K 33/44*    (2006.01)
*C01B 31/08*    (2006.01)
*C01B 31/02*    (2006.01)
*B01J 20/20*    (2006.01)

(52) U.S. Cl.
USPC ........... 424/125; 423/460; 423/461; 502/418; 502/416

(58) Field of Classification Search
USPC .................. 424/125; 423/460, 461; 502/416, 502/418
See application file for complete search history.

(56) References Cited

U.S. PATENT DOCUMENTS

| | | | |
|---|---|---|---|
| 4,822,765 A * | 4/1989 | Nishimura | 502/418 |
| 5,556,622 A * | 9/1996 | Uehara et al. | 424/125 |
| 5,576,261 A | 11/1996 | Sudhaker et al. | 502/185 |
| 5,977,016 A | 11/1999 | Von Blücher et al. | 502/426 |
| 5,993,766 A | 11/1999 | Tom et al. | 423/294 |
| 6,184,177 B1 | 2/2001 | Von Blücher et al. | 502/34 |
| 6,300,276 B1 | 10/2001 | De Ruiter et al. | 502/437 |
| 7,160,369 B2 * | 1/2007 | von Blucher et al. | 96/132 |
| 7,288,504 B2 | 10/2007 | Von Blücher et al. | 502/432 |
| 2003/0092560 A1 | 5/2003 | Von Blucher et al. | 502/10 |
| 2004/0141963 A1 * | 7/2004 | Umekawa et al. | 424/125 |
| 2004/0237790 A1 * | 12/2004 | von Blucher et al. | 96/154 |
| 2008/0118425 A1 | 5/2008 | DeRuiter | 423/447.2 |
| 2008/0171648 A1 | 7/2008 | Von Blucher et al. | 502/9 |

FOREIGN PATENT DOCUMENTS

| | | |
|---|---|---|
| CN | 1634761 A | 7/2005 |
| DE | 43 04026 A1 | 2/1993 |
| DE | 43 28 219 A1 | 2/1995 |
| DE | 196 00 237 A1 | 7/1996 |
| DE | 196 25 069 A1 | 1/1998 |
| DE | 199 30 732 A1 | 1/2001 |
| EP | 0 688 566 B1 | 12/2000 |
| EP | 0688 568 B1 | 4/2002 |
| EP | 1 500 397 A1 | 1/2005 |
| EP | 1 525 886 A1 | 4/2005 |
| EP | 1 547 605 A1 | 6/2005 |
| EP | 1 440 692 B1 | 12/2005 |
| EP | 1 745 792 A1 | 1/2007 |
| EP | 1 745 793 A1 | 1/2007 |
| EP | 1 748 031 A1 | 1/2007 |
| JP | 10-072208 | 3/1998 |
| JP | 2006-256882 | 9/2006 |
| WO | WO 98/07655 | 2/1998 |
| WO | WO 01/83368 A1 | 11/2001 |
| WO | WO 02/32569 A1 | 4/2002 |

OTHER PUBLICATIONS

European Council of Chemical Manufacturers' Federations, Test Methods for Activated Carbons, Item 1.6 "Mechanical Hardness", pp. 18-19, Nov. 1986.
Lowell, S., et al., Characterization of Porous Solids and Powders: Surface Area, Pore Size and Density, Particle Technology Series, vol. 16, pp. 111-112, $1^{st}$ ed., Kluwer Academic Publishers, 2004.
Winnacker-Kuchler ($3^{rd}$ edition), vol. 7, pp. 93 seq.
Z. Anal. Chem. 238, pp. 187-193 (1968).

* cited by examiner

*Primary Examiner* — Ernst Arnold
*Assistant Examiner* — Hong Yu
(74) *Attorney, Agent, or Firm* — Brannon Sowers & Cracraft PC

(57) ABSTRACT

The invention relates to the use of a particulate active carbon, in particular in the form of active carbon particles, preferably active carbon beads, for the field of medicine and/or for the production of a medicament, wherein the active carbon employed has a large micropore volume content, based on the total pore volume of the active carbon. A microporous active carbon of this type if particularly suitable for medicinal use.

8 Claims, No Drawings ent Application No. DE 10 2005 061 120.6, filed Dec. 19, 2005, and also to German Patent Application No. DE 10 2005 062 160.0, filed Dec. 22, 2005, entitled "ACTIVATED CARBON FOR MEDICAL USE". Both of these references are expressly incorporated by reference herein, in their entirety.

BACKGROUND OF THE INVENTION

The present invention relates to the area of active carbon (i.e. activated carbon) for medicinal use. In particular, the present invention relates to the use of a particulate active carbon having high microporosity for human medicinal or veterinary medicinal use. In addition, the present invention relates to a pharmaceutical composition which contains a particulate active carbon of this type and is suitable for human medicinal or veterinary medicinal use.

Active carbon, in particular in the form of "medicinal carbon" is administered in the field of medicine, in particular for the adsorption of poisonous substances, bacteria, gases etc. in the gastrointestinal tract. Diarrhoeal complaints (diarrhoea) and poisoning are the main field of application. In the case of the administration of active carbon in poisoning, the active carbon prevents absorption, in the case of poisoning with substances which are subject to an enterohepatic circulation (e.g. carbamazepine, phenobarbital, phenylbutazone, theophylline etc.), and leads to an acceleration of their elimination.

For further details on the medicinal use of active carbon, reference can be made, for example, to Römpp Chemielexikon [Römpp's Chemical Encyclopaedia], 10th Edition, Georg Thieme Verlag, Stuttgart/New York, keywords: "Active carbon" and "Medicinal carbon", and to Pschyrembel Medizinisches Wörterbuch [Pschyrembel's Medical Dictionary], 257th Edition, 1993, Nikol Verlagsgesellschaft mbH Hamburg, keyword: "Active carbon", and the literature in each case reviewed there.

For the medicinal fields of application of acute diarrhoea, for the prevention of absorption in the case of oral poisoning and for the acceleration of excretion in poisoning with substances which are subject to an enterohepatic circulation, commercially available preparations based on pulverulent medicinal active carbon in the form of "comprettes" are available. The pulverulent active carbon available, however, does not always offer optimal performance characteristics for the aforementioned fields of application.

In addition, active carbon in the form of spherical particles having sizes of 0.05 to 2 mm have already been proposed for other medicinal uses, namely for the treatment of haemorrhoidal complaints (EP 0 688 566 B1), for the treatment of inflammatory diseases of the bowel such as, for example, Crohn's disease or ulcerative colitis (EP 0 688 567 B1) and also for the treatment of peripheral inflammation of the stoma (EP 0 688 568 B1). However, even the spherical active carbon described in the aforementioned publications does not always fulfil the demands which are made on a medicinal active carbon.

The active carbon prepared from phenolic resin beads by carbonization and subsequent activation according to EP 1 440 692 B1 also does not always fulfil the desired demand profile which is made on a medicinal active carbon.

BRIEF SUMMARY

Use of a particulate active carbon for the field of medicine or for the production of a medicament is disclosed, wherein the active carbon employed has a large micropore volume content, based on the total pore volume of the active carbon.

It is therefore an object of the present invention to discover or to make available an active carbon which can be used in the field of human or veterinary medicine, which at least largely avoids or else at least reduces the previously described disadvantages of the prior art.

In particular, an object of the present invention is the discovery or making available of an active carbon or of a medicinal carbon which has good use properties in the field of medicine, in particular human or veterinary medicine.

DETAILED DESCRIPTION

For the purposes of promoting an understanding of the disclosure, reference will now be made to the embodiments described and specific language will be used to describe the same. It will nevertheless be understood that no limitation of the scope of the disclosure is thereby intended, such alterations and further modifications in the device and its use, and such further applications of the principles of the disclosure as illustrated therein being contemplated as would normally occur to one skilled in the art to which the disclosure relates.

The applicant has now surprisingly found that the previously described problem can be solved by an active carbon having a large micropore volume content, based on the total pore volume of the active carbon.

The subject of the present invention—according to a first aspect of the present invention—is thus the use of a particulate active carbon, in particular in the form of active carbon particles, preferably active carbon beads, for the field of medicine, in particular human or veterinary medicine, or for the production of a medicament for medicinal use (i.e. human or veterinary medicinal use), where the active carbon employed has a large micropore volume content, based on the total pore volume of the active carbon.

The applicant has surprisingly discovered that particulate, in particular granular, preferably spherical active carbon having a large micropore volume content has a particularly good medicinal activity, and this is true for various fields of application of medicine. When in the context of the present invention the field of medicine is discussed, both the field of human medicine and the field of veterinary medicine are always to be understood by this.

Without wanting to be committed to a specific theory, the particular effectiveness of the particulate active carbon having a large micropore volume content employed according to the invention can be attributed to the fact that such an active carbon can particularly efficiently adsorb poisonous substances, micro-organisms, such as bacteria and viruses, harmful gases and the like, since the micropores can interact with the adsorbates over the entire pore wall and can particularly effectively adsorb these.

On account of these properties, the active carbon employed according to the invention is particularly effective, in particular in comparison to products customary in the market, and consequently has to be employed in only lower doses than commercially available active carbon preparations.

When the question is of a large volume content of micropores in the context of the present invention, by the term micropores those pores within the active carbon are meant which have pore diameters ≦25 Å (2.5 nm), in particular ≦20 Å (2.0 nm).

The active carbon used according to the invention is suitable for the treatment of a number of complaints in humans and animals. In particular, the active carbon employed according to the invention is suitable for the treatment of complaints of the gastrointestinal tract or for the production of a medicament for treating complaints of the gastrointestinal tract. For example, the active carbon used according to the invention can be employed for the treatment of inflammatory complaints of the gastrointestinal tract, in particular bacterial or viral complaints of the gastrointestinal tract. For example, the active carbon employed according to the invention can be employed for the treatment of inflammatory, in particular bacterially or virally related complaints of the small and/or large intestine, in particular of enterocolitis. Furthermore, the active carbon used according to the invention can be employed for the treatment of diarrhoeal complaints (diarrhoea). Finally, the active carbon employed according to the invention can be employed for the treatment of poisoning, in particular food poisoning or poisoning after peroral assimilation of toxic substances. Thus, the active carbon employed according to the invention can prevent the absorption of the poisons by the body in the case of oral poisoning and in the case of poisoning with substances which are subject to an enterohepatic circulation (e.g. carbamazepine, phenobarbital, phenylbutazone, theophylline etc.), can accelerate their excretion and/or elimination.

The main field of application of the active carbon employed according to the invention is diarrhoeal complaints (diarrhoea) and poisoning.

For purposes of its medicinal use, the active carbon employed according to the invention is customarily administered perorally. For this purpose, the particulate, in particular spherical, active carbon can either be administered as such or else brought into a special administration form (e.g. capsules etc.).

The amounts administered depend on the type of indication or use: While in the treatment of poisoning approximately 0.1 to 5 g of active carbon/kg of body weight, in particular 0.2 to 2 g of active carbon/kg of body weight, are employed, in the other aforementioned indications a total of 100 mg to 5,000 mg, in particular 200 to 4,500 mg, preferably 500 to 4,000 mg, are administered perorally daily. In spite of this, it may be necessary to depart from the aforementioned amounts, namely depending on the body weight or on the type of administration, on individual behaviour, on the manner of formulation and on the time or interval at which administration takes place. Thus, in some cases it can be sufficient to manage with less than the aforementioned minimum amount, while in other cases the upper limit mentioned has to be exceeded. Customarily, it is advisable to divide administrations over a defined period of time, namely advantageously, for example, into a number of individual doses.

Preferably, the active carbon employed according to the invention consists of discrete active carbon particles, preferably discrete active carbon beads. The active carbon particles, preferably active carbon beads, here have mean particle diameters in the range from 0.01 to 2.0 mm, in particular 0.05 to 1.0 mm, preferably 0.1 to 1.0 mm. Particularly advantageously, an active carbon is used which is particularly mechanically stable and has a bursting pressure of at least 5 Newtons, in particular a bursting pressure in the range from 5 Newtons to 20 Newtons, per active carbon particle or active carbon bead.

According to the invention, the active carbon preferably employed has a raw density in the range from 700 to 975 g/cm³, in particular 750 to 950 g/cm³, preferably 800 to 900 g/cm³. Furthermore, it has a total porosity of 40 to 70%, in particular 45 to 65%, preferably 50 to 60%.

According to the invention, the active carbon preferably employed has a specific total pore volume in the range from 0.1 to 2.5 cm³/g, in particular 0.2 to 2.0 cm³/g, preferably 0.3 to 1.5 cm³/g, particularly preferably 0.4 to 1.0 cm³/g. Here, the content of pores having pore diameters ≦36 Å is advantageously at least 65%, in particular at least 70%, preferably at least 75%, and can be up to 95%, in particular up to 90%.

For medicinal use, it is particularly advantageous if the active carbon employed has a specific surface area (BET surface area) of at least 500 g/m², in particular at least 750 g/m², preferably at least 1,000 g/m², particularly preferably at least 1200 g/m². Customarily, the active carbon employed has a specific surface area (BET surface area) in the range from 500 to 2,500 g/m², in particular 750 to 2,250 g/m², preferably 900 to 2,000 g/m², particularly preferably 1,000 to 1,750 g/m². The aforementioned BET values relate to pores having pore diameters up to 400 Å inclusive. For the BET method, reference can be made, for example, to Römpp Chemielexikon [Römpp's Chemical Encyclopaedia], 10th Edition, Georg Thieme Verlag, Stuttgart/New York, keyword: "BET method", and the literature reviewed there, Winnacker-Küchler (3rd Edition), Volume 7, pages 93 ff. and Z. Anal. Chem. 238, pages 187 to 193 (1968).

In general, the active carbon employed according to the invention has an adsorption volume $V_{ads}$ of at least 250 cm³/g, in particular at least 300 cm³/g, preferably at least 350 cm³/g, particularly preferably at least 400 cm³/g. In general, the adsorption volume $V_{ads}$ of the active carbon employed is in the range from 250 to 1,000 cm³/g, in particular 300 to 900 cm³/g, preferably 350 to 750 cm³/g. The aforementioned values relate to a measurement of the adsorption volume at a partial pressure $p/p_0$ of 0.995 on pores having pore diameters in the range up to 400 Å inclusive.

Preferably, the active carbon employed has a total pore volume according to Gurvich of at least 0.50 cm³/g, in particular at least 0.55 cm³/g, preferably at least 0.60 cm³/g, particularly preferably at least 0.65 cm³/g, very particularly preferably at least 0.70 cm³/g. In general, the active carbon employed has a total pore volume according to Gurvich of 0.50 to 0.90 cm³/g, in particular 0.55 to 0.85 cm³/g, preferably 0.60 to 0.80 cm³/g, particularly preferably 0.65 to 0.80 cm³/g, very particularly preferably 0.70 to 0.75 cm³/g. The aforementioned values relate to the determination at a partial pressure $p/p_0$ of 0.995 on pores having a pore diameter up to 400 Å inclusive. For further details with respect to the determination of the total pore volume according to Gurvich, reference can be made to L. Gurvich (1915), J. Phys. Chem. Soc. Russ. 47, 805, and to S. Lowell et al., Characterization of Porous Solids and Powders: Surface Area Pore Size and Density, Kluwer Academic Publishers, Article Technology Series, pages 111 ff.

All physicochemical data of the active carbon indicated below equally relate to measurements on pores having pore diameters in the range of from >0 Å up to 400 Å.

As described beforehand, a feature of the active carbon employed according to the invention can be seen in its particularly high micropore volume content. As defined beforehand, the term micropores designates those pores having pore diameters of ≦25 Å, in particular ≦20 Å. Consequently, the term micropore volume content designates that volume content which is made available by pores having pore diameters of ≦25 Å, in particular ≦20 Å. In the active carbon employed according to the invention, the content of the micropore volume, based on the total pore volume of the active carbon, is at least 60%, in particular at least 65%, preferably at least 70%. In general, the micropore volume content of the active carbon employed, based on the total pore volume of the active carbon, is in the range from 60 to 95% by weight, in particular 65 to 90% by weight, preferably 70 to 85% by weight. Investigations of the applicant have shown that a microporous active carbon of this type is surprisingly particularly suitable for medicinal use, in particular it has a particularly good medicinal activity.

In general, the active carbon employed according to the invention has a micropore volume, in particular a micropore volume formed from pores having pore diameters of $\leq 25$ Å, preferably $\leq 20$ Å, according to Carbon Black of at least 0.40 $cm^3/g$, in particular at least 0.45 $cm^3/g$, preferably at least 0.50 $cm^3/g$. In general, the micropore volume of the active carbon employed (i.e. the micropore volume formed from pores having pore diameters of $\leq 25$ Å, preferably $\leq 20$ Å) according to Carbon Black is in the range from a 0.40 to 0.80 $cm^3/g$, in particular 0.45 to 0.75 $cm^3/g$, preferably 0.50 to 0.6 $cm^3/g$. For further details of the determination of the pore surface area according to Carbon Black, reference can be made, for example, to R. W. Magee, Evaluation of the External Surface Area of Carbon Black by Nitrogen Adsorption, Presented at the Meeting of the Rubber Division of the American Chem. Soc., October 1994, e.g. reviewed in: Quantachrome Instruments, AUTOSORB-1, AS1 Win Version 1.50, Operating Manual, P/N 05061, Quantachrome Instruments 2004, Florida, USA, pages 71 ff.

In addition to a particularly high micropore volume content, the active carbon employed according to the invention also has a particularly high micropore surface area content with respect to the total pore surface area. In general, the active carbon employed according to the invention, based on the specific total surface area (BET) of the active carbon, has a specific micropore surface area content (i.e. a specific micropore surface area content formed from pores having pore diameters of $\leq 25$ Å, preferably $\leq 20$ Å) of at least 70%, in particular at least 75%, preferably at least 80%, very particularly preferably at least 85%. In general, the specific micropore surface area content, based on the specific total surface area (BET), is in the range from 70 to 95%, preferably 75 to 95%, very particularly preferably 80 to 90%.

In general, the active carbon employed according to the invention has a micropore surface area according to Carbon Black (i.e. a micropore surface area according to Carbon Black formed from pores having pore diameters of $\leq 25$ Å, preferably $\leq 20$ Å) of at least 400 $g/m^2$, in particular at least 800 $g/m^2$, preferably at least 1,000 $g/m^2$, particularly preferably at least 1,200 $g/m^2$. In general, the micropore surface area according to Carbon Black is in the range from 400 to 1,750 $g/m^2$, in particular 800 to 1,500 $g/m^2$, preferably 1,000 to 1,400 $g/m^2$, particularly preferably 1,100 to 1,300 $g/m^2$.

As a result of its high microporosity, the active carbon employed according to the invention preferably has a median pore diameter (average pore diameter) of at most 35 Å, preferably at most 30 Å, particularly preferably at most 25 Å. In general, the median pore diameter (average pore diameter) of the active carbon employed according to the invention is in the range from 15 to 35 Å, in particular 15 to 30 Å, preferably 20 to 25 Å.

The applicant has surprisingly discovered that an active carbon which is obtainable by carbonization and subsequent activation of styrene/divinylbenzene copolymers, in particular divinylbenzene-crosslinked polystyrenes, preferably in granular form, particularly preferably in spherical form, is particularly efficacious in the context of the present invention; in particular, good use results are obtained with a divinylbenzene content of the styrene/divinylbenzene copolymers employed as starting materials for the active carbon preparation in the range from 1 to 15% by weight, preferably 2 to 10% by weight, based on the styrene/divinylbenzene copolymers. For example, an active carbon of this type of an active carbon prepared starting from phenolic resin beads (cf., for example, EP 1 440 692 B1) is superior in its action.

Active carbon employable according to the invention, which fulfils the aforementioned requirements and/or specifications containing the aforementioned physico-chemical requirements is marketed, for example, by Blücher GmbH, Erkrath, Germany, and also Adsor-Tech GmbH, Premnitz, Germany.

An active carbon of this type is prepared by means of carbonization carried out under conditions known per se and subsequent activation of suitable microporous starting materials, preferably based on divinyl-benzene-crosslinked styrene resin beads. This is familiar to the person skilled in the art, so that no further details need to be mentioned regarding this.

According to a further aspect of the present invention, the present invention relates to a pharmaceutical composition which comprises a particulate active carbon, in particular in the form of active carbon particles, preferably in the form of active carbon beads, the active carbon having a large micropore volume content, based on the total pore volume of the active carbon. With respect to further details of the active carbon employed in the pharmaceutical composition according to the invention, reference can be made to the above remarks, which apply accordingly with respect to the pharmaceutical composition.

The term pharmaceutical composition is to be understood very broadly in the context of the present invention and includes every type of possible pharmaceutical composition, in particular medicaments or pharmaceuticals as such, but also medicinal products, homoeopathic agents, food supplements etc.

In addition to the active carbon, the pharmaceutical composition according to the invention can moreover include a pharmacologically acceptable vehicle or excipient and/or pharmacologically acceptable vehicles and/or excipients.

The pharmaceutical composition according to the invention is present in the form of a perorally administrable administration form, in particular in the form of capsules, tablets, pellets, comprettes, pills etc. In general, the pharmaceutical composition contains the active carbon per application unit, in particular per tablet, capsule, comprette, pellet, pill or the like, in amounts of 100 mg to 1,000 mg.

Further embodiments, modifications and variations of the present invention are recognizable and realizable without problems for the person skilled in the art on reading the description, without him here leaving the context of the present invention.

The present invention is illustrated with the aid of the Example below, which is in no case intended to restrict the present invention.

EXAMPLE

Thirty patients with acute diarrhoeal complaints (diarrhoea) as a result of a gastrointestinal infection were treated with active carbon, ten patients receiving an active carbon employed according to the invention, while of the other twenty subjects ten subjects received a commercially available medicinal active carbon based on active carbon powder in the form of comprettes (Comparison I), and a spherical active carbon, which was prepared from phenolic resin beads according to EP 1 440 692 B1 (Example 1, median particle diameter of about 0.1 mm), was administered to the remaining ten subjects (Comparison II).

The active carbon employed according to the invention, which was employed as such in the form of active carbon beads, was obtained from Adsor-Tech GmbH, Premnitz, Germany, and is prepared by carbonization and subsequent activation of spherical styrene/divinyl-benzene copolymer particles (divinylbenzene content of about 5% by weight, based on the styrene/divinyl-benzene copolymers); the active carbon employed according to the invention has the following properties:

- active carbon beads having median particle diameters of about 0.4 to 0.6 mm
- bursting pressure per active carbon bead: >5 Newtons
- BET total surface area: about 1,400 m$^2$/g
- adsorption volume V$_{ads}$ (p/p$_0$=0.995): about 470 cm$^3$/g
- total pore volume according to Gurvich: about 0.72 cm$^3$/g
- micropore volume content $\leq$20 Å, based on the total pore volume up to 400 Å: about 70%
- micropore volume $\leq$20 Å according to Carbon Black: about 0.51 cm$^3$/g
- micropore surface area content, based on BET total surface area: about 89%
- micropore surface area $\leq$20 Å according to Carbon Black: about 1,250 m$^2$/g
- median pore diameter (average pore diameter): about 21 Å
- raw density: about 0.87 to 0.89 g/cm$^3$
- specific total pore volume: about 0.64 to 0.66 cm$^3$/g
- specific pore volume $\leq$36 Å: about 0.50 to 0.56 cm$^3$/g In the ten patients who received the commercially available medicinal active carbon based on an active carbon powder in the form of active carbon comprettes (Comparison I), the therapy had to be carried out for five days with daily total doses of about 4,000 mg/day until a therapeutic success occurred.

In the ten patients to whom the spherical active carbon which was prepared from phenolic resin beads according to EP 1 440 692 B1 was administered (Comparison II), the therapy also had to be carried out for five days using daily total doses of about 4,000 mg/day until a therapeutic success occurred.

However, in the case of the microporous active carbon used according to the invention in the form of active carbon beads of the type described beforehand based on styrene/divinyl-benzene copolymers (Adsor-Tech) the therapy in the ten patients treated with the active carbon employed according to the invention was already complete after three days, and this with a total daily dose of active carbon of only about 2,000 mg/day.

The preceding investigations show the improved efficiency of the active carbon employed according to the invention based on microporous active carbon beads based on styrene/divinylbenzene copolymers both in comparison to the commercially available medicinal active carbon and in comparison to phenolic resin-based active carbon.

The present investigations verify the improved efficacy of particulate, in particular granular or spherical active carbon having a high microporosity, i.e. large micropore volume and large micropore surface content, based on styrene/divinylbenzene copolymers (i.e. the active carbon is obtained by carbonization and subsequent activation of these styrene/divinylbenzene copolymers).

While the preferred embodiment of the invention has been illustrated and described in the foregoing description, the same is to be considered as illustrative and not restrictive in character, it being understood that all changes and modifications that come within the spirit of the invention are desired to be protected.

The invention claimed is:

1. Pharmaceutical composition for the treatment of complaints of the gastrointestinal tract, the pharmaceutical composition comprising a particulate active carbon in the form of active carbon particles in the form of active carbon beads or spherules,
    wherein the active carbon is obtained by carbonization and subsequent activation of styrene/divinylbenzene copolymers,
    wherein the active carbon has a total pore volume according to Gurvich in the range of from 0.50 to 0.90 cm$^3$/g and wherein the active carbon has a micropore volume content formed from pores having pore diameters of $\leq$25 Å of at least 70%, based on the total pore volume of the active carbon, and wherein the active carbon has an average pore diameter of at most 30 Å,
    wherein the pharmaceutical composition is present in the form of a perorally administrable administration form,
    wherein the pharmaceutical composition contains a pharmacologically acceptable excipient and comprises the active carbon in amounts of from 100 mg to 1,000 mg per administrative unit; and
    wherein the pharmaceutical composition is in a form selected from the group consisting of capsules, tablets, pellets, comprettes and pills.

2. The pharmaceutical composition according to claim 1, wherein the active carbon employed comprises discrete active carbon particles, the active carbon particles having a bursting pressure of at least 5 Newtons per particle.

3. The pharmaceutical composition according to claim 1, wherein the active carbon employed is a spherical active carbon having median particle diameters in the range from 0.01 to 2.0 mm.

4. The pharmaceutical composition according to claim 1, wherein the active carbon employed has a specific surface area (BET surface area) in the range of from 500 to 2,500 m$^2$/g.

5. The pharmaceutical composition according to claim 1, wherein the active carbon employed has an adsorption volume V$_{ads}$ in the range of from 250 to 1,000 cm$^3$/g.

6. The pharmaceutical composition according to claim 1, wherein the active carbon employed has a content of the micropore volume, based on the total pore volume of the active carbon, in the range of from 60 to 95%.

7. The pharmaceutical composition according to claim 1, wherein the active carbon employed has a micropore volume determined according to Carbon Black method and formed from pores having pore diameters of $\leq$25 Å in the range of from of 0.40 to 0.80 cm$^3$/g.

8. The pharmaceutical composition according to claim 1, wherein the active carbon employed, based on the specific total surface area (BET) of the active carbon, has a specific micropore surface area content formed from pores having pore diameters of $\leq$25 Å in the range of from of 70 to 95%.

* * * * *